(12) United States Patent
Trost et al.

(10) Patent No.: US 10,881,545 B2
(45) Date of Patent: Jan. 5, 2021

(54) PENILE TRACTION DEVICES

(71) Applicants: Mayo Foundation for Medical Education and Research, Rochester, MN (US); PathRight Medical Inc., Wayzata, MN (US)

(72) Inventors: Landon W. Trost, Rochester, MN (US); Jason Gerold, Shakopee, MN (US); Zachary M. Hoffman, Bloomington, MN (US); David Talen, Plymouth, MN (US)

(73) Assignees: Mayo Foundation for Medical Education and Research, Rochester, MN (US); PathRight Medical Inc., Wayzata, MN (US)

( * ) Notice: Subject to any disclaimer, the term of this patent is extended or adjusted under 35 U.S.C. 154(b) by 123 days.

(21) Appl. No.: 16/307,802

(22) PCT Filed: Jun. 7, 2017

(86) PCT No.: PCT/US2017/036291
§ 371 (c)(1),
(2) Date: Dec. 6, 2018

(87) PCT Pub. No.: WO2017/214235
PCT Pub. Date: Dec. 14, 2017

(65) Prior Publication Data
US 2019/0209359 A1   Jul. 11, 2019

Related U.S. Application Data

(60) Provisional application No. 62/347,316, filed on Jun. 8, 2016.

(51) Int. Cl.
*A61F 5/41*   (2006.01)
*A61F 5/00*   (2006.01)

(52) U.S. Cl.
CPC ............... *A61F 5/41* (2013.01); *A61F 5/00* (2013.01); *A61F 2005/411* (2013.01); *A61F 2005/414* (2013.01)

(58) Field of Classification Search
CPC ......................................................... A61F 5/41
(Continued)

(56) References Cited

U.S. PATENT DOCUMENTS 8,734,324 B2   5/2014 Muller
10,117,771 B2   11/2018 Trost et al.
(Continued)

FOREIGN PATENT DOCUMENTS

DE   20203927   7/2002
EP   1473000    11/2004

OTHER PUBLICATIONS

Arafa et al., "The prevalence of Peyronie's disease in diabetic patients with erectile dysfunction," Int J Impot Res., 19(2):213-217, Epub Aug. 17, 2006.
(Continued)

*Primary Examiner* — John P Lacyk
(74) *Attorney, Agent, or Firm* — Fish & Richardson P.C.

(57) ABSTRACT

Devices and methods for treating penile aberrations include the use of traction devices. For example, this document describes devices and methods for applying longitudinal and/or contralateral penile traction forces to treat anatomical aberrations related to Peyronie's disease and other conditions.

15 Claims, 7 Drawing Sheets

(58) Field of Classification Search
USPC .................................................... 600/38–41
See application file for complete search history.

(56) References Cited

U.S. PATENT DOCUMENTS

| | | |
|---|---|---|
| 2004/0215055 A1 | 10/2004 | Gomez-de-Diego |
| 2005/0124854 A1 | 6/2005 | Suchy et al. |
| 2007/0016107 A1* | 1/2007 | Egydio .................. A61B 90/06 600/587 |
| 2009/0247377 A1 | 10/2009 | Ono |
| 2010/0204543 A1 | 8/2010 | Sanchez Martinez |
| 2011/0172489 A1 | 7/2011 | Muller |
| 2011/0213201 A1 | 9/2011 | Moon |
| 2012/0130158 A1 | 5/2012 | Deitch et al. |
| 2016/0235580 A1 | 8/2016 | Trost |

OTHER PUBLICATIONS

Chung et al., "Penile traction therapy and Peyronie's disease: a state of art review of the current literature," Ther Adv Urol., 5(1):59-65, Feb. 2013.

Dalkin et al., "Potent men undergoing radical prostatectomy: a prospective study measuring sexual health outcomes and the impact of erectile dysfunction treatments," Urol Oncol., 26(3):281-285, Epub Nov. 7, 2007.

Dibenedetti et al., "A Population-Based Study of Peyronie's Disease: Prevalence and Treatment Patterns in the United States," Adv Urol., 2011:282503. Epub Oct. 23, 2011.

Extended European Search Report in European Application No. 17810914.6 dated Jul. 5, 2019, 59 pages.

Gontero et al., A pilot phase-II prospective study to test the 'efficacy' and tolerability of a penile extender device in the treatment of 'short penis' BJU Int., Ju;y 9, 2008,101: 793-797.

La Pera et al., "Peyronie's disease: prevalence and association with cigarette smoking. A multicenter population-based study in men aged 50-69 years," Eur Urol., 40(5):525-530, Nov. 2001.

Lindsay et al., "The incidence of Peyronie's disease in Rochester, Minnesota, 1950 through 1984," J Urol., 146(4):1007-1009, Oct. 1991.

Martinez-Salamanca et al., "Acute phase Peyronie's disease management with traction device: a nonrandomized prospective controlled trial with ultrasound correlation," J Sex Med., 11(2):506-515, Epub Nov. 22, 2013.

Mulhall et al., "Subjective and objective analysis of the prevalence of Peyronie's disease in a population of men presenting for prostate cancer screening," J Urol., 171(6 Pt 1):2350-2353, Jun. 2004.

PCT International Search Report and Written Opinion in International Appln. Np. PCT/US17/36291, dated Aug. 26, 2017, 13 pages.

Rhoden et al., "Prevalence of Peyronie's disease in men over 50-y-old from Southern Brazil," Int J Impot Res., 13(5):291-293, Oct. 2001.

Rybak et al., "A retrospective comparative study of traction therapy vs. no traction following tunica albuginea plication or partial excision and grafting for Peyronie's disease: measured lengths and patient perceptions," J Sex Med., 9(9):2396-2403, Epub Aug. 17, 2012.

Schwarzer et al., "The prevalence of Peyronie's disease: results of a large survey," BJU Int., 88(7):727-730, Nov. 2001.

* cited by examiner

PENILE TRACTION DEVICES

CROSS-REFERENCE TO RELATED APPLICATIONS

This application is a National Stage application under 35 U.S.C. § 371 of International Application No. PCT/US2017/036291, having an International Filing Date of Jun. 7, 2017, which claims priority to U.S. Application Ser. No. 62/347,316, filed on Jun. 8, 2016. This disclosure of the prior applications are considered part of (and are incorporated by reference in) the disclosure of this application.

BACKGROUND

1. Technical Field

This document relates to devices and methods for treating penile aberrations. For example, this document relates to devices and methods for applying longitudinal and/or contralateral penile traction forces to treat anatomical aberrations related to Peyronie's disease and other conditions.

2. Background Information

Peyronie's disease is the development of fibrous scar tissue inside the penis that causes curved, painful erections. In some cases, Peyronie's disease causes a significant bend or pain. This can prevent a man from having sex or might make it difficult to get or maintain an erection (erectile dysfunction or ED). For many men, Peyronie's disease also causes stress and anxiety. In a small percentage of men, Peyronie's disease goes away on its own. But in most cases, it will remain stable or worsen. Treatment might be needed if the curvature is severe enough that it prevents successful sexual intercourse.

Peyronie's disease signs and symptoms might appear suddenly or develop gradually. The most common signs and symptoms of Peyronie's disease include: scar tissue that can be felt under the skin of the penis as flat lumps or a band of hard tissue, a significant bend to the penis, a narrowing or an hourglass appearance, problems attaining or maintaining an erection, shortening of the penis, and pain, with or without an erection.

SUMMARY

This document provides devices and methods for treating penile aberrations. For example, this document provides devices and methods for applying longitudinal and/or contralateral penile traction forces to treat anatomical aberrations related to Peyronie's disease and other conditions.

In one implementation, a penile traction device for applying traction force to a penis of a human body includes a base with a surface configured for interfacing with the human body while the traction force is applied to the penis; a longitudinally-adjustable portion extending from the base; and a pivotable portion extending from the longitudinally-adjustable portion. The longitudinally-adjustable portion is spring-loaded for applying a longitudinal traction force to the penis. The pivotable portion is selectively pivotable in relation to the longitudinally-adjustable portion. The pivotable portion includes a clamp for releasably clamping a distal portion of the penis to the penile traction device.

Such a penile traction device may optionally include one or more of the following features. The base may define a clearance hole through which the penis can extend. The longitudinally-adjustable portion may include: a first stage of longitudinal length adjustability; and a second stage of longitudinal length adjustability. The first stage of longitudinal length adjustability may be adjustable in length independent of the second stage of longitudinal length adjustability. The second stage of longitudinal length adjustability may include one or more springs such that the longitudinally-adjustable portion is spring-loaded. The second stage of longitudinal length adjustability may include a mechanism for releasably latching the second stage of longitudinal length adjustability in a retracted configuration. While the second stage of longitudinal length adjustability is latched in the retracted configuration, the one or more springs may be inactive such that the one or more springs do not apply the longitudinal traction force. While the second stage of longitudinal length adjustability is unlatched from the retracted configuration, the one or more springs may actively apply the longitudinal traction force. The one or more springs may apply the longitudinal traction force in a direction perpendicular to the surface of the base. The pivotable portion may be selectively pivotable in relation to the longitudinally-adjustable portion along a range of adjustment of 120 degrees. The pivotable portion may be detainable in three or more differing angular relationships in relation to the longitudinally-adjustable portion.

In another implementation, a method of applying one or more types of traction force to a penis include: (1) coupling a penile traction device of any type provided herein to the penis; and applying the one or more types of traction force to the penis using the device.

Such a method of applying one or more types of traction force to a penis may optionally include one or more of the following features. The traction force may be applied subsequent to coupling the device to the penis. The traction force may be a dynamic-loading traction force.

Particular embodiments of the subject matter described in this document can be implemented to realize one or more of the following advantages. In some embodiments, the devices described herein are configured to concurrently apply longitudinal traction forces to induce gradual penile lengthening. In some embodiments, the devices described herein are configured to concurrently apply longitudinal and lateral traction forces. Hence, reduction of penile curvature and increase in penile length can result from the use of a single traction device. In some embodiments, the devices described herein are configured for applying progressive mechanical traction. That is, the devices are adjustable so as to progressively add traction forces to allow for gradual and on-going anatomical improvements. In some embodiments, the devices described herein are configured to exert traction forces that are readily adjustable. Hence, definitive treatment plans can be ordered and implemented, thereby potentially enhancing patient results. In some embodiments, the devices described herein are configured to be worn comfortably and discreetly. In addition, in some embodiments the devices described herein are configured to allow measurement and tracking of anatomical improvements over time. Such features can provide feedback regarding patient compliance and results to the treatment provider and give the patient motivation to adhere to the treatment protocol. In some embodiments, the devices described herein can be used advantageously in conjunction with a pharmacological agent as part of a treatment plan for Peyronie's disease and other conditions.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

Figure 1:
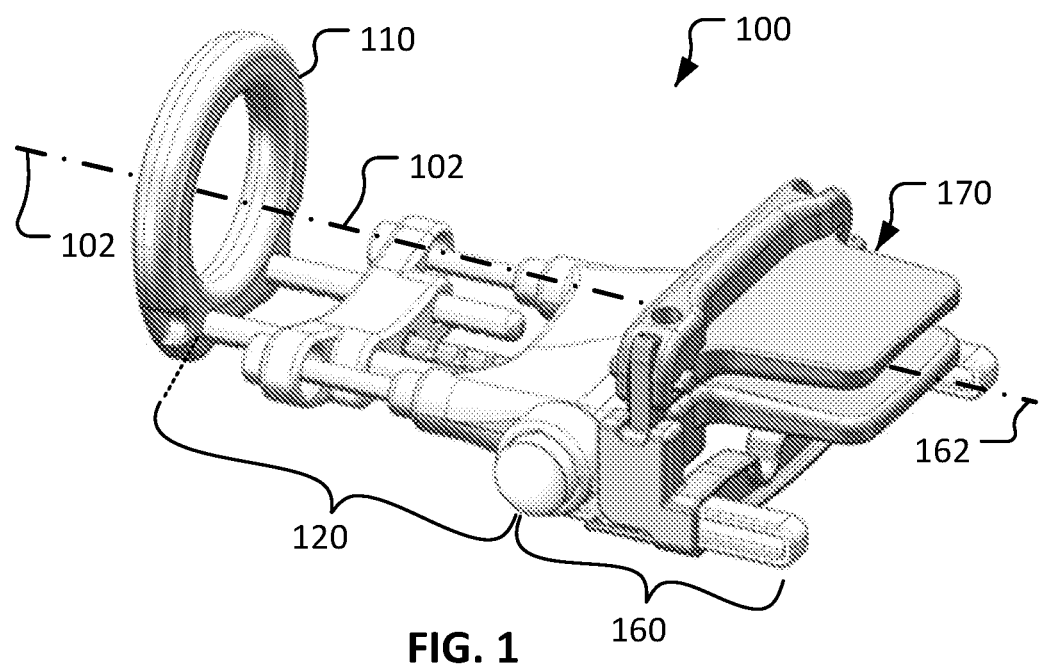
FIG. 1 is a perspective view of an example penile traction device in accordance with some embodiments provided herein.

This document provides devices and methods for treating penile aberrations. For example, this document provides devices and methods for applying longitudinal and/or contralateral penile traction forces to treat anatomical aberrations related to Peyronie's disease and other conditions. For example, the devices provided herein can be used for treatment of decreased penile length pertaining to Peyronie's disease. Further, treatment directed to penile curvature reduction while undergoing intralesional therapies for Peyronie's disease can be delivered using the devices and methods provided herein. In some circumstances, the devices provided herein are beneficial for use pre-operatively or during post-operative recovery following surgical treatment of Peyronie's disease or other urological conditions such as prostate cancer.

In general, the treatment algorithm for Peyronie's disease can include the use of a penile traction device. The goal of such therapy is to increase penile length or at a minimum restore length that was previously lost to the disease state. This is useful in men with Peyronie's disease, as a loss of penile length is commonly one of their biggest complaints. Traction therapy can be used in all phases of treatment including prior to or following surgery, during or after injection treatments, or as a stand-alone therapy.

There are also other indications for the use of penile traction therapy. One such use is for reducing penile curvature, either as a standalone therapy or in combination with injections and/or surgery. The known currently available traction devices do not permit contralateral application of force, and hence, they are only applying force in the longitudinal direction. Another indication for the penile traction devices provided herein would be for men scheduled to undergo placement of a penile prosthesis. Use of a penile traction device may increase the overall length of the patient's anatomy possible allowing for a larger prosthesis to be inserted, and also potentially make the surgery itself easier. A third indication is to use the traction devices as a stand-alone therapy. Many men complain of decreased penile length, particularly among those experiencing erectile dysfunction from any one of several known contributing conditions (diabetes, following prostatectomy, vascular disease, and others), and this therapy has been shown to increase length without need for other procedures.

The devices described herein will address Peyronie's without treatment, Peyronie's with intralesional treatment, or even patients seeking a restoration or enhancement of penile length. In addition, the devices provided herein can be useful for applying penile traction in combination with a drug regimen (e.g., XIAFLEX®) to treat penile curvature.

As described further below, in some embodiments the traction force(s) applied are dynamic loads. That is, as the penis stretches in response to the traction force(s), additional traction force(s) continue to be applied. This is in contrast to stretching and holding the traction force(s) applicators (e.g., clamp) at a fixed location(s).

Figure 2:
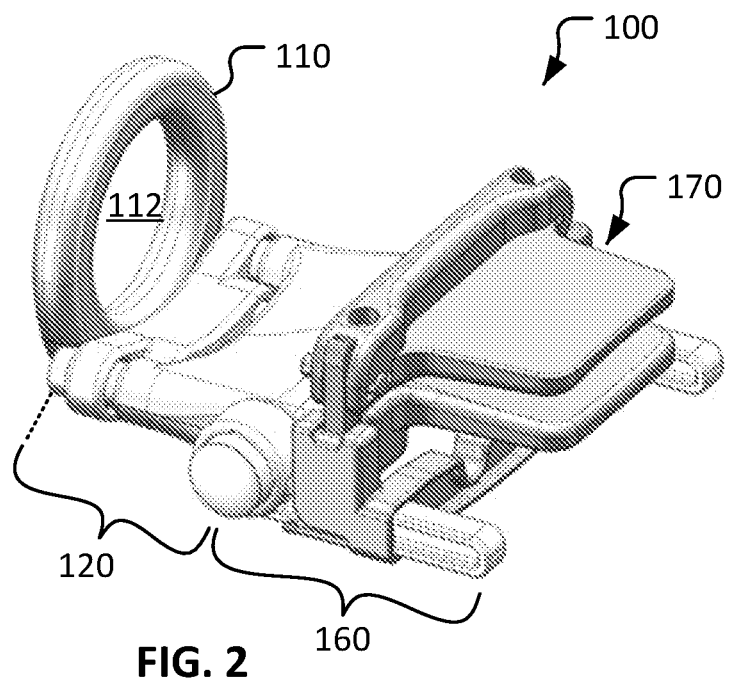
FIG. 2 is a perspective view of the penile traction device of FIG. 1 in a longitudinally retracted configuration.

With reference to FIGS. 1 and 2, an example penile traction device 100 can be used to provide penile length modification and/or to treat penile aberrations. Such aberrations may be related to, but are not necessarily exclusively related to, Peyronie's disease. In some implementations, the aberrations of penis may be, but are not limited to, decreased penile length and/or excessive penile curvature. In some embodiments, penile traction device 100 is configurable to treat both conditions, i.e., to treat both decreased penile length and/or excessive penile curvature. Penile traction device 100 is also configurable to treat either one of decreased penile length or excessive penile curvature.

In the depicted embodiment, penile traction device 100 includes a base 110, a longitudinally-adjustable portion 120, and a pivotable portion 160. Base 110 is disposed at the proximal end of penile traction device 100; pivotable portion 160 is disposed at the distal end of penile traction device 100; and longitudinally-adjustable portion 120 is disposed between base 110 and pivotable portion 160. In this context, "proximal" means towards the user, while "distal" means away from the user.

In some embodiments, various components of penile traction device 100 are readily interchangeable with replacement components that can differ in size, material properties, shape, and the like. In some embodiments, penile traction device 100 can be assembled in two or more manners, or can be otherwise adjustable, so as to facilitate customization for various users.

Base 110 and longitudinally-adjustable portion 120 define a first longitudinal axis 102. While penile traction device 100 is being worn by a user, a proximal portion of the user's penis is generally parallel to first longitudinal axis 102.

Pivotable portion 160 defines a second longitudinal axis 162. While penile traction device 100 is being worn by a user, a distal portion of the user's penis is generally parallel to second longitudinal axis 162.

In some cases, while the arrangement of penile traction device 100 is as shown in FIGS. 1 and 2, first longitudinal axis 102 is substantially parallel with second longitudinal axis 162. In some cases, the arrangement of penile traction device 100 is such that a shallow angle is maintained between first longitudinal axis 102 and second longitudinal axis 162. Having a shallow angle between axes 102 and 162 may be more comfortable than having axes 102 and 162 be parallel, in some cases. For example, without limitation, in some cases an angle between axes 102 and 162 is in a range of about 0° to about 5°, or about 1° to about 4°, or about 2° to about 3°, or about 0° to about 10°.

However, as described further below, since pivotable portion 160 is selectively pivotable in relation to longitudinally-adjustable portion 120 (and base 110), in some arrangements of penile traction device 100 first longitudinal axis 102 is not parallel with second longitudinal axis 162. In some such arrangements, first longitudinal axis 102 is coplanar but not parallel with second longitudinal axis 162. In some such arrangements, first longitudinal axis 102 and longitudinal axis 162 are skew in relation to each other.

While penile traction device 100 is worn by a user, a proximal surface of base 110 abuts the user's abdomen. Base 110 defines an open area 112 through which the user's penis can pass. In the depicted embodiment, base 110 comprises a generally circular ring shape. In some embodiments, without limitation, base 110 can comprise a U-shape, V-shape, ovular shape, and the like.

In some embodiments, base 110 is made of one or more polymeric material(s). Some example materials that can be used to construct base 110 include, but are not limited to, DELRIN®, polystyrene, acrylonitrile butadiene styrene, polyvinyl chloride, polyethylene, high density polyethylene, low density polyethylene, polypropylene, polycarbonate, polyphenelyne ether, polyamide (PA or Nylon), ultra high molecular weight polyethylene, polyimide, polyetherimide, polyphenylene sulfide, polyurethane, polyetheretherketone, thermoplastic copolyether (PEBAX), Fluorinated Ethylene Propylene, and combinations thereof.

Alternatively, base 110 can be made of metals such as aluminum, stainless steel, titanium, and the like, and alloys thereof. Further, in some embodiments coated metals are used for base 110. For example, in some embodiments silicon-coated aluminum is used as the construct for base 110. It should be understood that the forgoing materials are just some example materials that can be used to make base 110, and that other materials (e.g., graphite, natural materials, etc.) are also within the envisioned scope of this disclosure.

Longitudinally-adjustable portion 120 extends distally from base 110. In the depicted embodiment, longitudinally-adjustable portion 120 extends generally orthogonally from base 110. In some embodiments, longitudinally-adjustable portion 120 extends from base 110 at a non-orthogonal angle (e.g., about 80°-90°, about 70°-80°, about 60°-70°, about 50°-60°, or about 40°-50°, and the like).

As described further below, longitudinally-adjustable portion 120 extends distally from base 110 by a user-adjustable distance. For example, in the arrangement shown in FIG. 1 longitudinal adjustable portion 120 extends distally by a longer distance than the arrangement shown in FIG. 2. What is more, as described further below, a portion of longitudinally-adjustable portion 120 is spring-loaded along axis 102 such that longitudinally-adjustable portion 120 can apply a dynamic longitudinal traction force to the user's penis. Longitudinally-adjustable portion 120 includes two stages of longitudinal length adjustability, as described further below.

Longitudinally-adjustable portion 120, without limitation, can be constructed of any of the materials listed above in reference to base 110.

Pivotable portion 160 includes a clamp 170. Clamp 170 is configured to releasably couple a distal portion of the user's penis to penile traction device 100. Clamp 170 includes opposing clamping surfaces that are contoured, smooth, and amply sized so that clamp 170 provides a comfortable fit for the user with distributed pressure (without pressure points). Moreover, clamp 170 is adjustable, as described further below.

Pivotable portion 160, without limitation, can be constructed of any of the materials listed above in reference to base 110.

Figure 3:
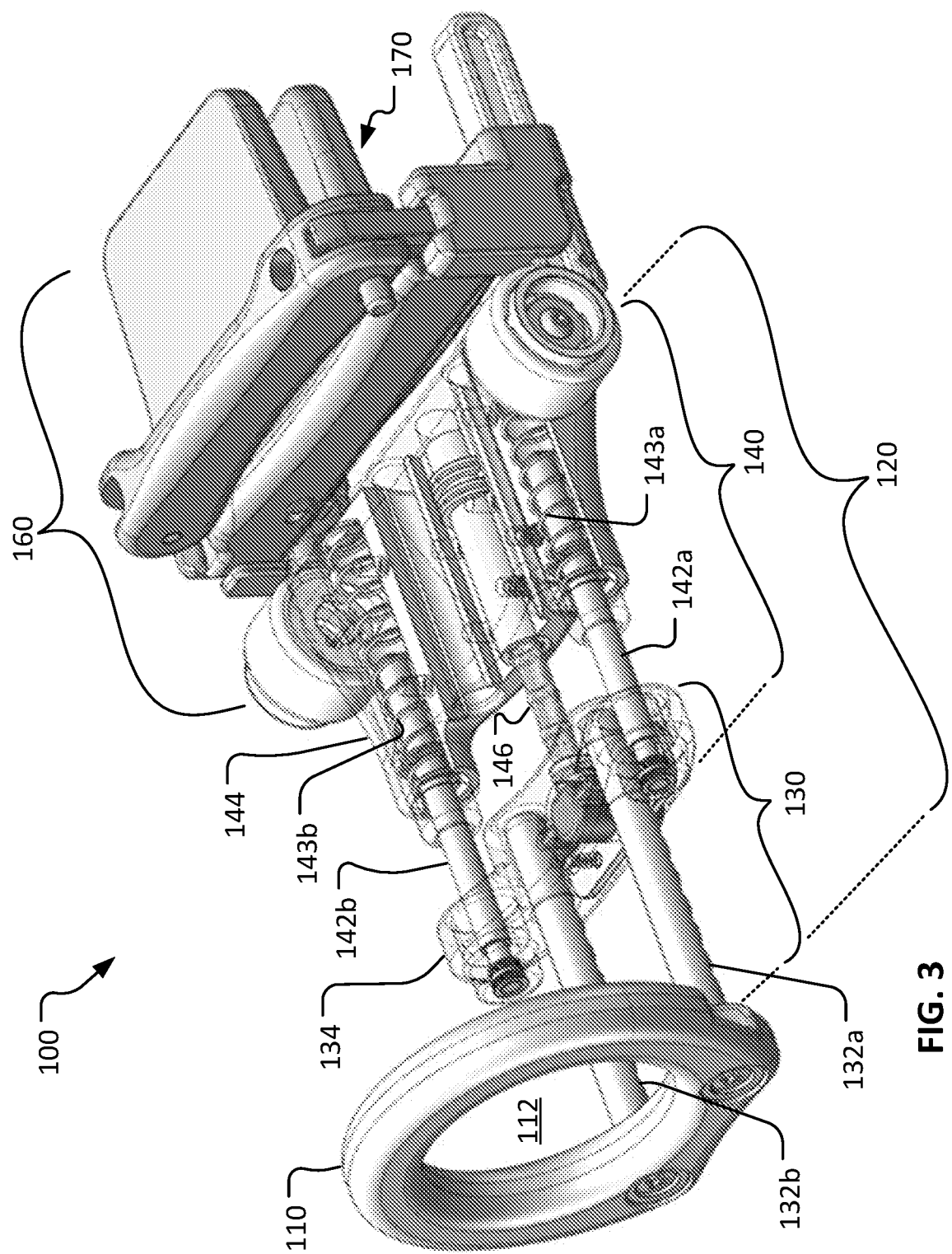
FIG. 3 is a perspective view of the penile traction device of FIG. 1 in a longitudinally extended configuration. Some components are transparent to facilitate visualization of other internal components.
Figure 4:
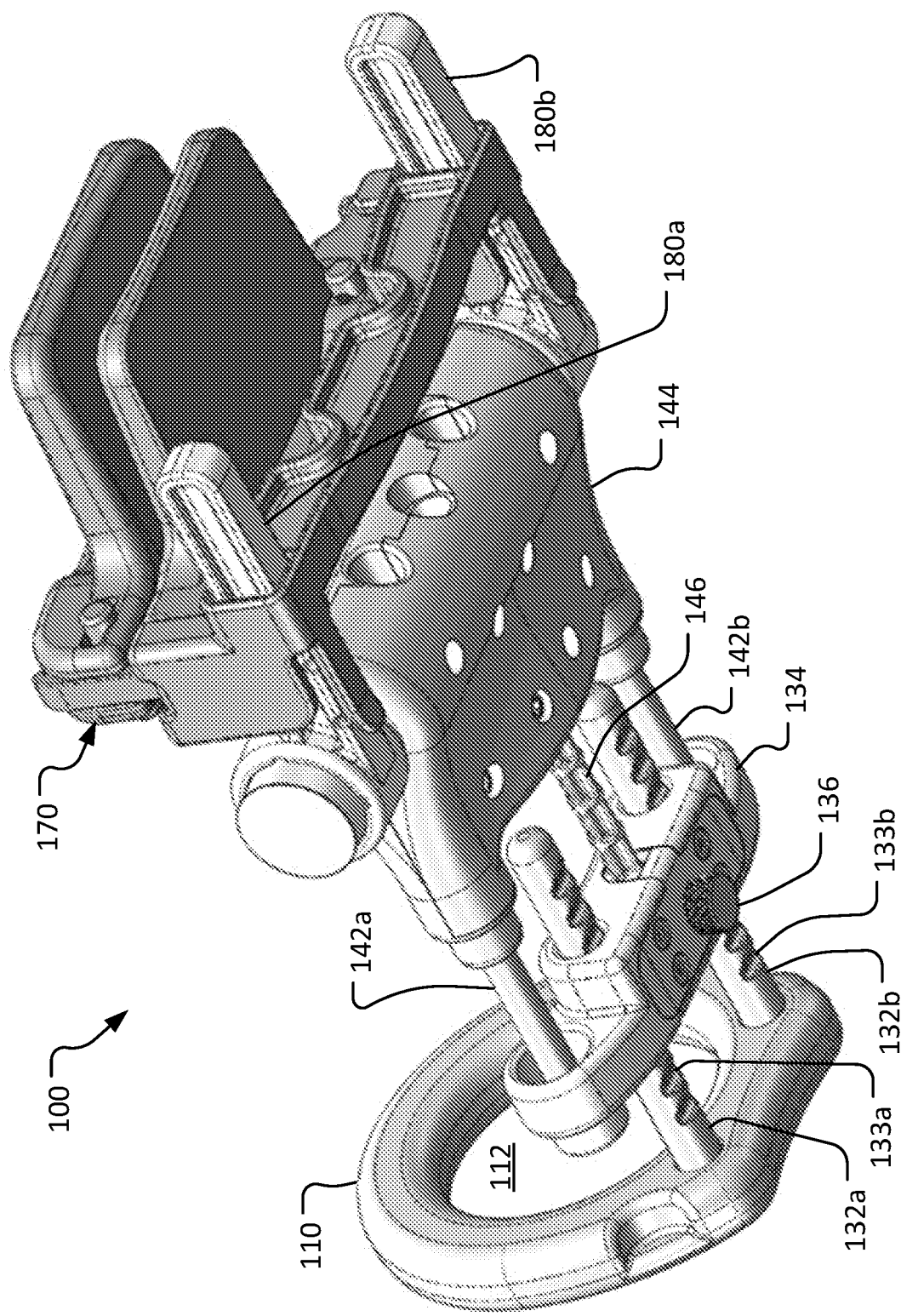
FIG. 4 is a perspective view of the penile traction device of FIG. 1 showing the underside of the device.

Referring also to FIGS. 3 and 4, longitudinally-adjustable portion 120 includes two stages of longitudinal length adjustability. That is, longitudinally-adjustable portion 120 includes a first stage of longitudinal length adjustability 130 and a second stage of longitudinal length adjustability 140. In the depicted embodiment, first stage of longitudinal length adjustability 130 extends directly from base 110 in a distal direction, and second stage of longitudinal length adjustability 140 extends from first stage of longitudinal length adjustability 130 in a distal direction. Hence, longitudinally-adjustable portion 120 can be described as having a telescoping length adjustability.

It should be understood that, in FIG. 3, some components are depicted transparently so that internal components are visible.

First stage of longitudinal length adjustability 130 includes a first extension rod 132a, a second extension rod 132b, and a yoke 134. Yoke 134 is slidably coupled with first and second extension rods 132a and 132b, and is configured to releasably latch in a plurality of longitudinal positions along the lengths of first and second extension rods 132a and 132b.

First and second extension rods 132a and 132b extend distally from base 110. In some embodiments, base 110 is configured with multiple mounting holes to accommodate the mounting of first and second extension rods 132a and 132b at various locations on base 110. For example, base 110 can include four mounting holes, six mounting holes, eight mounting holes, ten mounting holes, twelve mounting holes, or more than twelve mounting holes to accommodate the mounting of first and second extension rods 132a and 132b at various locations around the periphery of base 110.

In the depicted embodiment, first and second extension rods 132a and 132b are linear. In some embodiments, first and second extension rods 132a and 132b can have one or more curves. For example, in some embodiments first and second extension rods 132a and 132b can have curved proximal end portions such that first and second extension rods 132a and 132b are mounted higher on base 110 and extend from the base 110 at a downward incline.

First and second extension rods 132a and 132b of various lengths can be used to accommodate various anatomical sizes. In some cases, a kit that includes a variety of differing first and second extension rods 132a and 132b with different lengths can be provided.

Yoke 134 can be configured to releasably latch in a plurality of longitudinal positions along the lengths of first and second extension rods 132a and 132b. For example, in the depicted embodiment, first and second extension rods 132a and 132b, include a series of notches 133a and 133b, respectively, in a plurality of longitudinal positions along the lengths of first and second extension rods 132a and 132b.

In the depicted embodiment, yoke 134 includes a transversely-oriented toothed member that releasably engages with notches 133a and 132b. The transversely-oriented toothed member is manipulable by a knob 136 that is coupled with the transversely-oriented toothed member. In the depicted embodiment, the transversely-oriented toothed member and knob 136 is spring-biased towards yoke 134 such that the transversely-oriented toothed member is naturally biased to be engaged with notches 133a and 133b. When knob 136 is pulled away from yoke 134, the transversely-oriented toothed member becomes disengaged from notches 133a and 133b. As knob 136 is retained in the position away from yoke 133, yoke 134 is free to be slid proximally and distally along first and second extension rods 132a and 132b. When knob 136 is released, then the transversely-oriented toothed member will become engaged with a pair of notches 133a and 133b. Hence, first stage of longitudinal length adjustability 130 is adjustable in that yoke 134 is slidable along first and second extension rods 132a and 132b toward and/or away from base 110. In some embodiments, first and second extension rods 132a and 132b can be separated from engagement with yoke 134 by pulling knob 136 away from yoke 134 and concurrently sliding first and second extension rods 132a and 132b out of engagement with yoke 134.

In some embodiments, the transversely-oriented toothed member that engages with notches 133a and 133b is transversely slidable in relation to yoke 134 so as to engage and disengage yoke 134 with first and second extension rods 132a and 132b. The transversely-oriented toothed member can define clearance areas that get positioned in alignment with first and second extension rods 132a and 132b while the transversely-oriented toothed member is transversely pressed. The transversely-oriented toothed member can be spring-biased to bounce back from being transversely pressed such that the transversely-oriented toothed member that reengages with notches 133a and 133b. In some embodiments, first and second extension rods 132a and 132b can be separated from engagement with yoke 134 by transversely pressing the transversely-oriented toothed member and concurrently sliding first and second extension rods 132a and 132b out of engagement with yoke 134.

In some embodiments, notches 133a and 133b are configured to allow distally-directed sliding of yoke 134 along first and second extension rods 132a without requiring manipulation of knob 136, while requiring manipulation of knob 136 to slide yoke 134 proximally. For example, the distal sides of notches 133a and 133b can be beveled to allow for notches 133a and 133b to become disengaged from notches 133a and 133b simply by the application of a distally-directed force to yoke 134. In some such embodiments, the distal-most notch 133a and 133b does not include the bevel. In some embodiments, the reverse arrangement can be incorporated. That is, in some embodiments notches 133a and 133b are configured to allow proximally-directed sliding of yoke 134 along first and second extension rods 132a without requiring manipulation of knob 136, while requiring manipulation of knob 136 to slide yoke 134 distally.

Second stage of longitudinal length adjustability 140 extends from first stage of longitudinal length adjustability 130 in a distal direction. Second stage of longitudinal length adjustability 140 includes three rods coupled to and extending distally from yoke 134: (i) a third extension rod 142a, (ii) a fourth extension rod 142b, and (iii) a compression lock mechanism rod 146. The rods 142a, 142b, and 146 slidably terminate within a tensioner sub assembly 144.

Within tensioner sub assembly 144 are two compression springs 143a and 143b. Compression spring 143a is slidably coupled with third extension rod 142a, and compression spring 143b is slidably coupled with fourth extension rod 142b. Compression springs 143a and 143b tend to bias tensioner sub assembly 144 distally away from yoke 134. It is these compression springs 143a and 143b that can apply a dynamic tensile force (i.e., a longitudinal traction force that adjusts along with adjustments in length of longitudinally-adjustable portion 120) to a penis while a user is wearing penile traction device 100.

Figure 5:
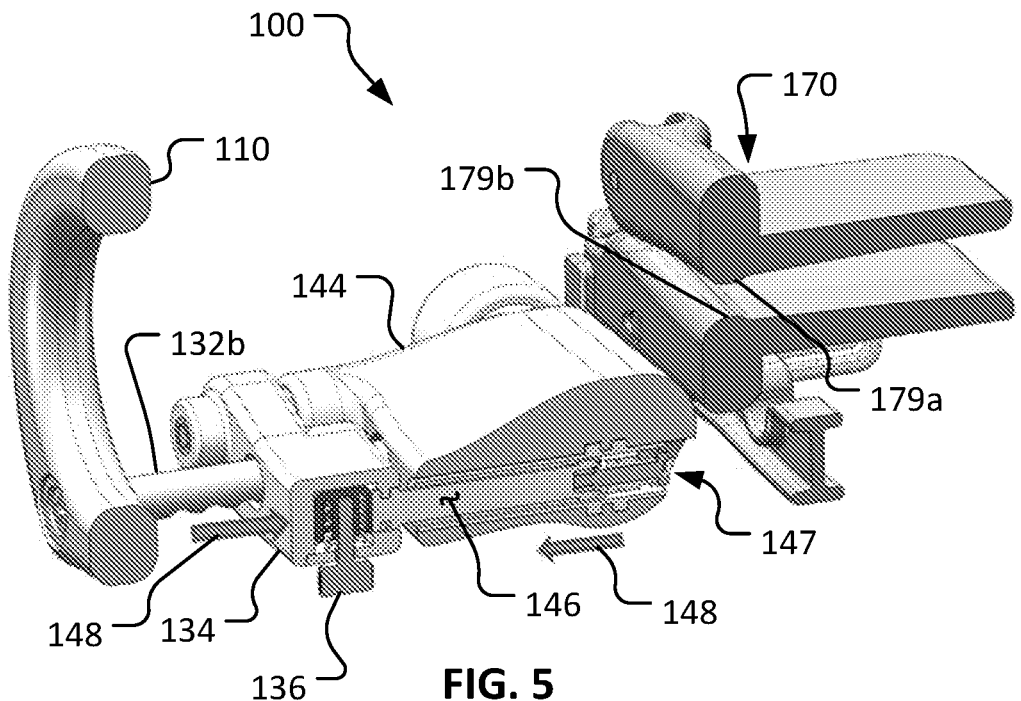
FIGS. 5 and 6 are longitudinal cross-sectional views of the penile traction device of FIG. 1 in partially retracted and partially extended configurations, respectively.
Figure 6:
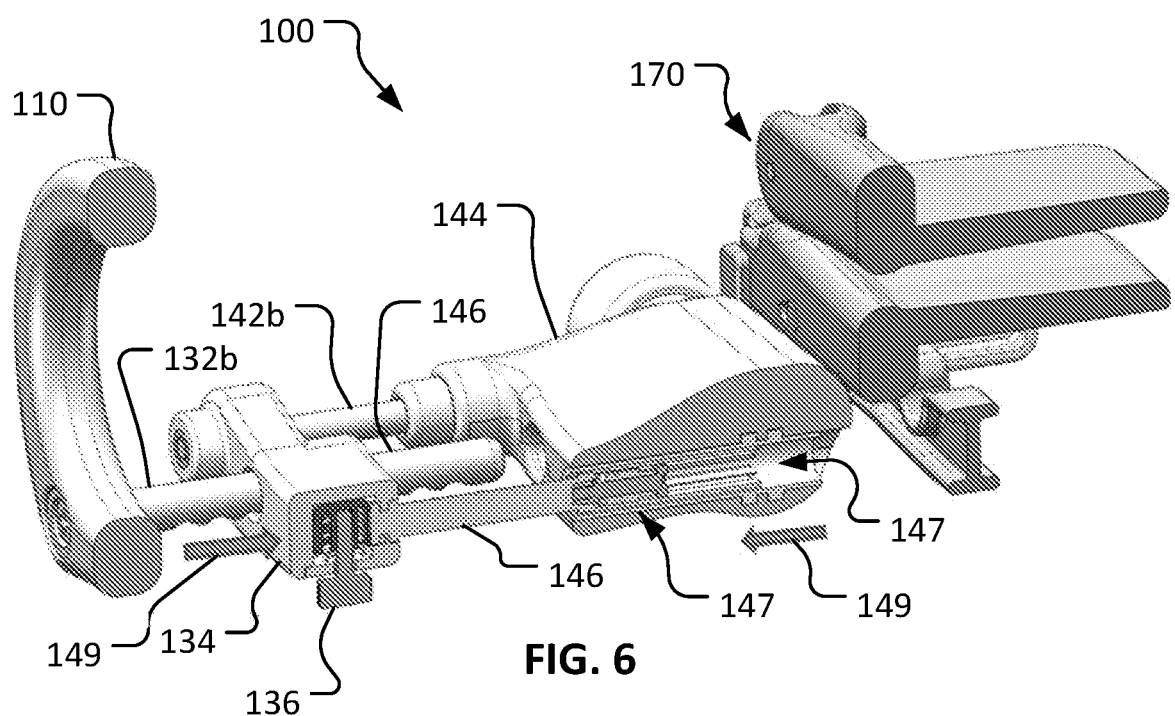
Figure 7:
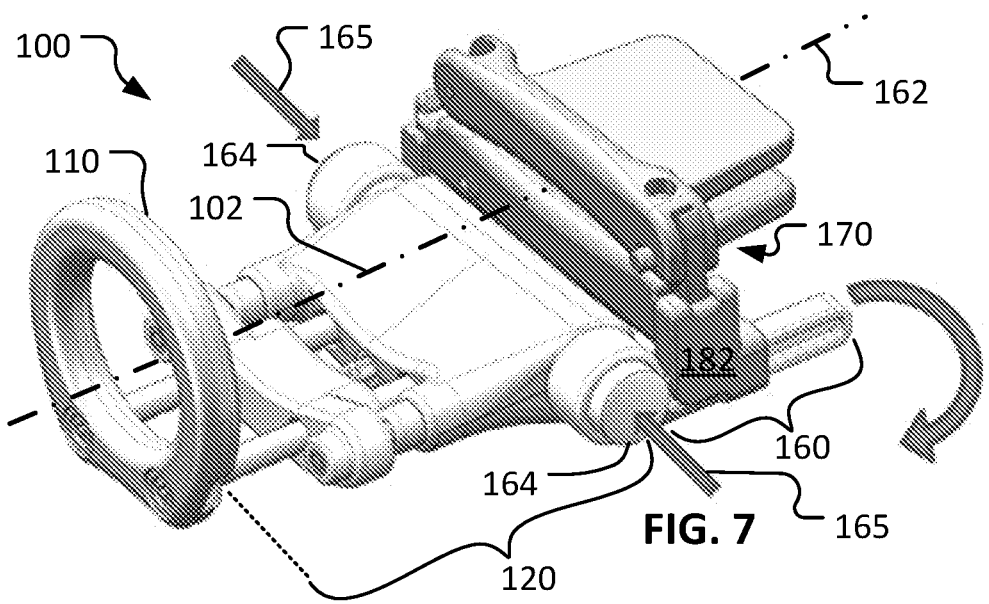
FIGS. 7-10 are a group of figures illustrating how a distal portion of the penile traction device of FIG. 1 is pivotable in relation to a proximal portion of the device.
Figure 8:
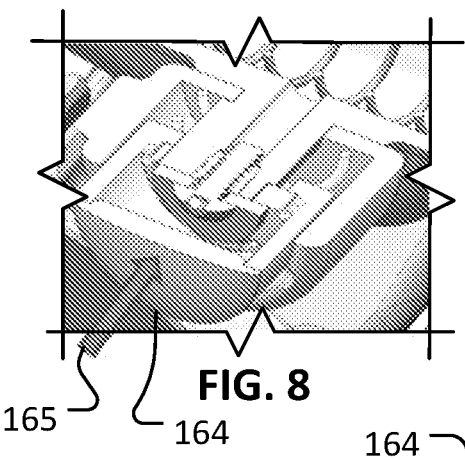

Referring also to FIGS. 5 and 6, compression lock mechanism rod 146 is part of a compression lock mechanism 147 of tensioner sub assembly 144 that can releasably detain second stage of longitudinal length adjustability 140 in a longitudinally retracted configuration. For example, second stage of longitudinal length adjustability 140 can be releasably detained in the configuration shown in FIG. 5. In that longitudinally retracted configuration, compression springs 143a and 143b are not active. That is, compression springs 143a and 143b are overcome by compression lock mechanism 147 because compression lock mechanism 147 is releasably detaining second stage of longitudinal length adjustability 140 in the longitudinally retracted configuration such that compression springs 143a and 143b are not able to apply tensile force to a penis while a user is wearing penile traction device 100.

To release second stage of longitudinal length adjustability 140 from being detained in its longitudinally retracted configuration, a compressive force can be applied between yoke 134 and tensioner sub assembly 144 as depicted by opposing arrows 148. In such an instance, compression lock mechanism 147 will then be released such that tensioner sub assembly 144 is free to extend distally under the influence of compression springs 143a and 143b, as depicted in FIG. 6. Thereafter, as depicted by opposing arrows 149, second stage of longitudinal length adjustability 140 can be once again be releasably detained in the longitudinally retracted configuration by compressively sliding tensioner sub assembly 144 towards yoke 134 to the configuration shown in FIG. 5. Compression lock mechanism 147 will releasably detain second stage of longitudinal length adjustability 140 in the configuration shown in FIG. 5. In some embodiments, compression lock mechanism 147 is analogous to the mechanism used in retractable ballpoint pens.

Referring to FIGS. 7-10, pivotable portion 160 is selectively pivotable in relation to longitudinally-adjustable portion 120. Pivotable portion 160 includes a first pivot arm 180a and a second pivot arm 180b (refer to FIG. 4).

Figure 9:
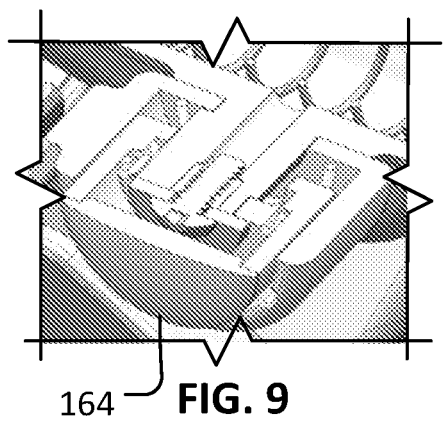

In order to pivot pivotable portion 160 in relation to longitudinally-adjustable portion 120, the user can apply opposing compressive forces (as indicated by arrows 165) to release buttons 164. While release buttons 164 are held in a compressed configuration (as shown in FIG. 9), pivotable portion 160 is free to be pivoted in relation to longitudinally-adjustable portion 120. In the depicted embodiment, release buttons 164 are spring-loaded such that, after the removal of compressive forces 165, release buttons 164 will spring back to their laterally-outward home positions where they can releasably latch pivotable portion 160 in a fixed angular relationship to longitudinally-adjustable portion 120.

Figure 10:
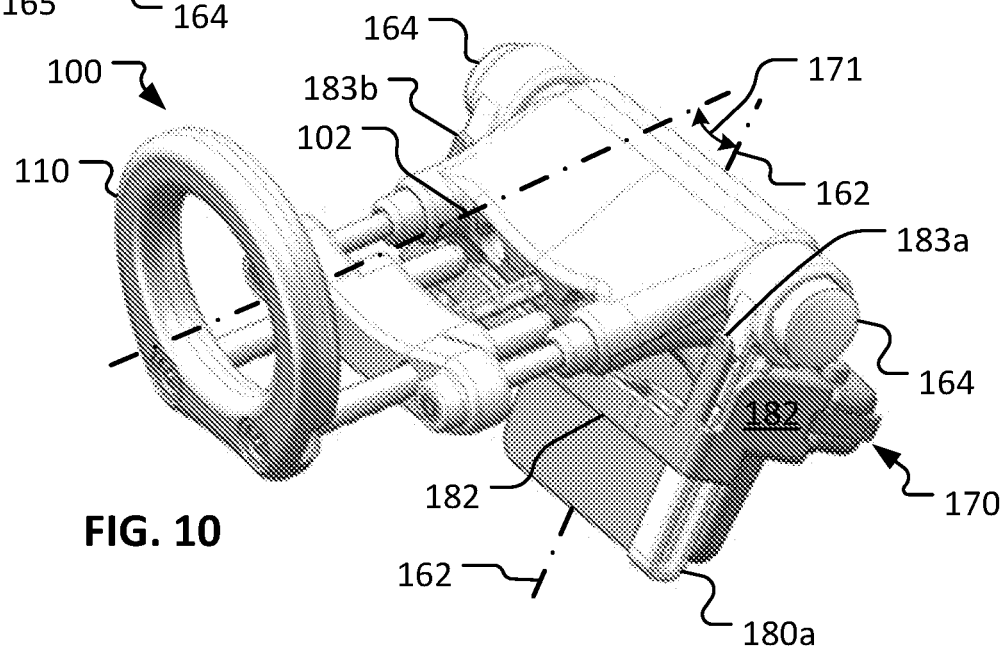

As pivotable portion 160 is pivoted in relation to longitudinally-adjustable portion 120, axis 102 of longitudinally-adjustable portion 120 becomes unparallel in relation to axis 162 of pivotable portion 160 (e.g., FIG. 10). Therefore, an angle 171 is defined between axis 102 and axis 162. In some embodiments, penile traction device 100 is configured such that pivotable portion 160 will releasably latch in relation to longitudinally-adjustable portion 120 at particular incremental degrees of angle 171. For example, in some embodiments angle 171 can be releasably latchable at about 15° increments between 0° and 120°. In some embodiments, angle 171 can be releasably latchable at about 20°, at about 30°, at about 45°, or at about 60° increments between 0° and 120° (or greater than 120° in some embodiments).

An adjustable clamp bracket 182 is slidably coupled to first pivot arm 180a and second pivot arm 180b. Adjustable clamp bracket 182 is also releasably coupled to clamp 170. In some embodiments, clamp 170 is releasably coupled to adjustable clamp bracket 182 using a deflectable tang or catch lever that can be manually deflected to allow clamp 170 to be released from being coupled to adjustable clamp bracket 182. Hence, adjustable clamp bracket 182 is an intermediary member that adjustably couples clamp 170 to first pivot arm 180a and second pivot arm 180b.

The orientation of adjustable clamp bracket 182 (and hence clamp 170) in relation to first pivot arm 180a and second pivot arm 180b is slidable adjustable along the longitudinal axes of first pivot arm 180a and second pivot arm 180b. To adjust adjustable clamp bracket 182 in relation to pivot arms 180a and 180b, in the depicted embodiment tabs 183a and 183b can be forced away from pivot arms 180a and 180b to disengage teeth of adjustable clamp bracket 182 from notches in pivot arms 180a and 180b. Then, while tabs 183a and 183b are held away from pivot arms 180a and 180b, adjustable clamp bracket 182 can be slid in relation to first pivot arm 180a and second pivot arm 180b.

In some embodiments, adjustable clamp bracket 182 can be retained in relation to pivot arms 180a and 180b using removable screws. To adjust the positioning of adjustable clamp bracket 182 in relation to pivot arms 180a and 180b, the screws can be removed, adjustable clamp bracket 182 can be moved to a desired position in relation to pivot arms 180a and 180b, and then the screws can be reinstalled to retain adjustable clamp bracket 182 in the desired position in relation to pivot arms 180a and 180b.

With adjustable clamp bracket 182 in a desired orientation in relation to pivot arms 180a and 180b, tabs 183a and 183b can be released and they will snap back into engagement with the notches in pivot arms 180a and 180b. In some embodiments, a series of multiple notches can be defined by first pivot arm 180a and second pivot arm 180b. Hence, adjustable clamp bracket 182 can be latched in relation to pivot arms 180a and 180b in any desired orientation of a multiple of different possible orientations.

Figure 11:
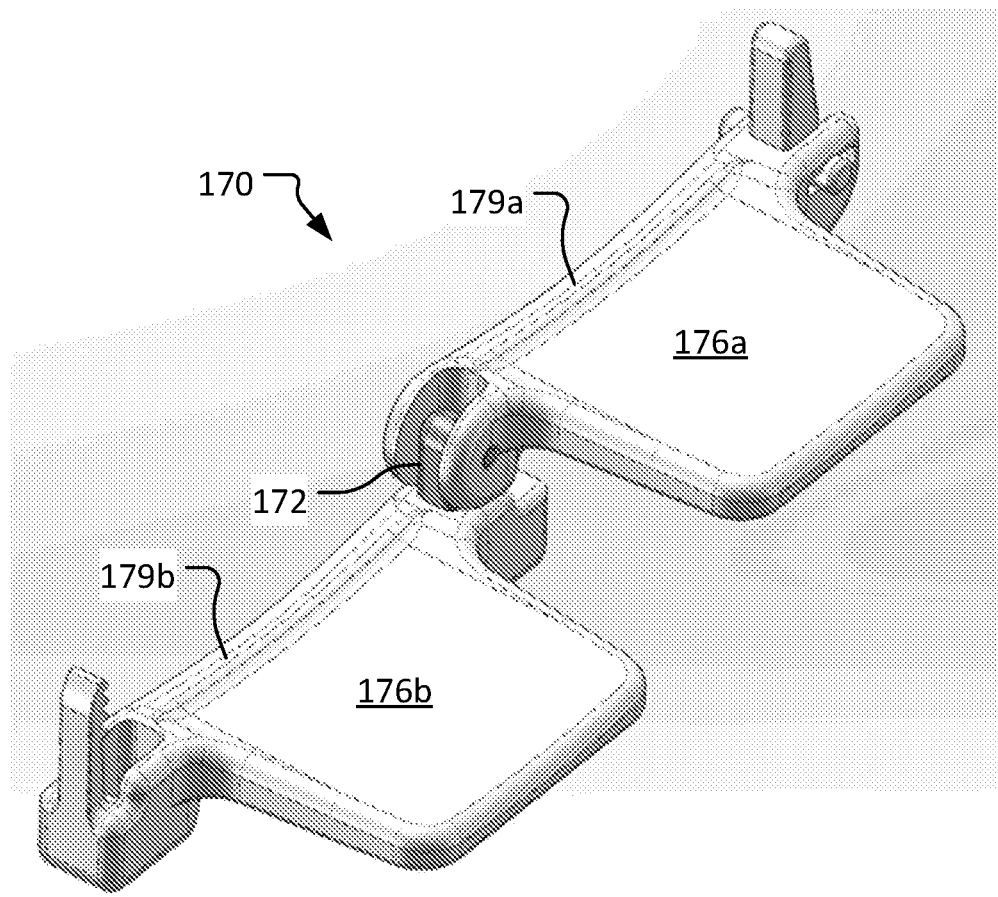
FIGS. 11-13 are a group of figures illustrating how the height of a hinged clamp of the penile traction device of FIG. 1 is adjustable.
Figure 12:
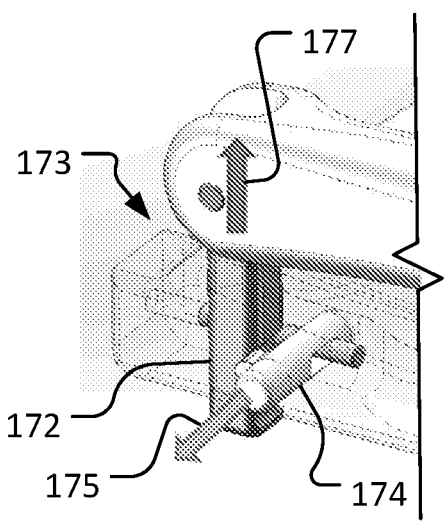
Figure 13:
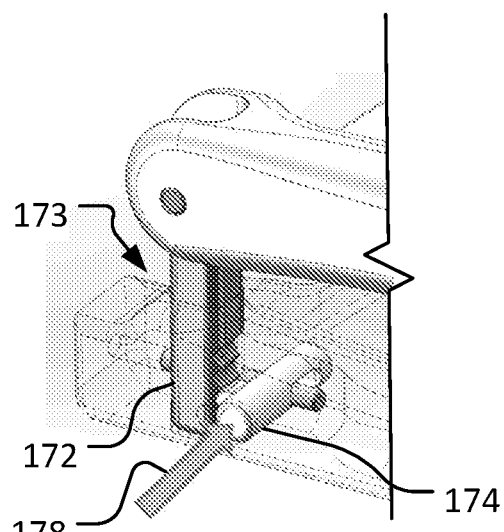

Referring to FIG. 11-13, in some embodiments clamp 170 is configured with an adjustable hinge pin 172. In the depicted embodiment, adjustable hinge pin 172 can be adjusted (e.g., height-wise), via a hinge pin height adjustment mechanism 173, to facilitate different clamping clearances between clamp members 176a and 176b.

Hinge pin height adjustment mechanism 173 can include a release member 174. In the depicted embodiment, when release member 174 is pulled (as depicted by arrow 175 in FIG. 12) adjustable hinge pin 172 is free to be moved upward and/or downward along its longitudinal axis (as depicted by arrow 176). Then, with adjustable hinge pin 172 in a desired location, release member 174 can be pushed (as depicted by arrow 178 in FIG. 13) to releasably detain adjustable hinge pin 172 in the desired location.

In some embodiments, clamp members 176a and 176b can include optional ridges 179a and 179b respectively (see also to FIG. 5). Such ridges 179a and 179b can help to retain the tissue while under tension in some cases. Ridges 179a and 179b are protrusions in comparison to other surface portions of clamp members 176a and 176b.

In some embodiments, clamp members 176a and 176b are large enough to allow the anatomy (glans) to be entirely captured within the length of the clamp 170.

Figure 14:
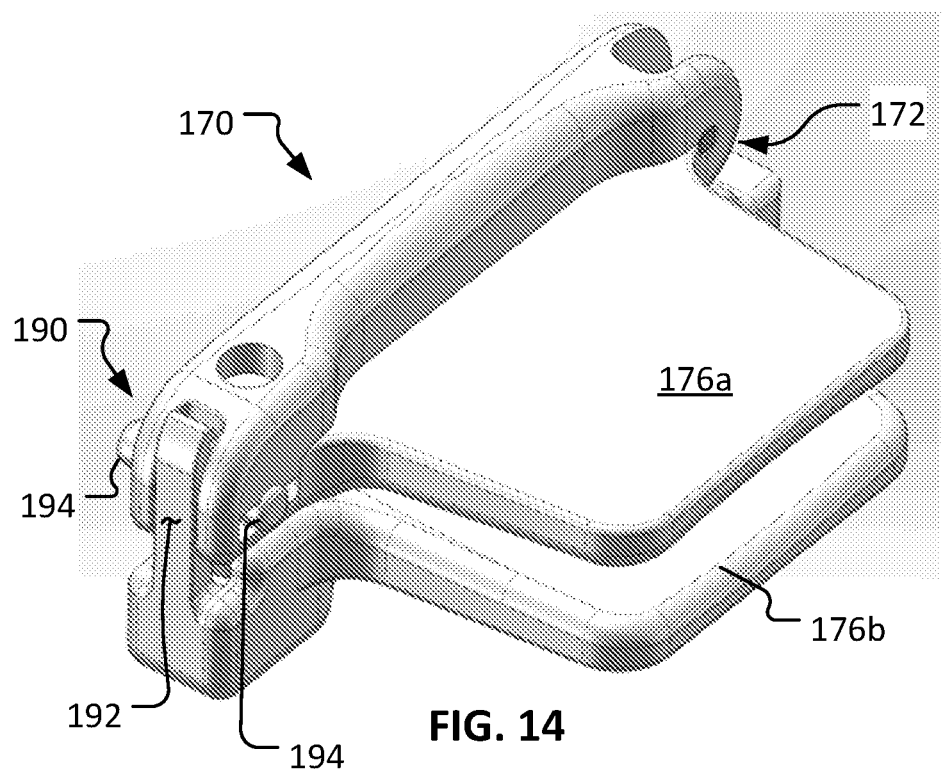
FIGS. 14 and 15 illustrate how a clamp of the penile traction device of FIG. 1 is releasably latchable.
Figure 15:
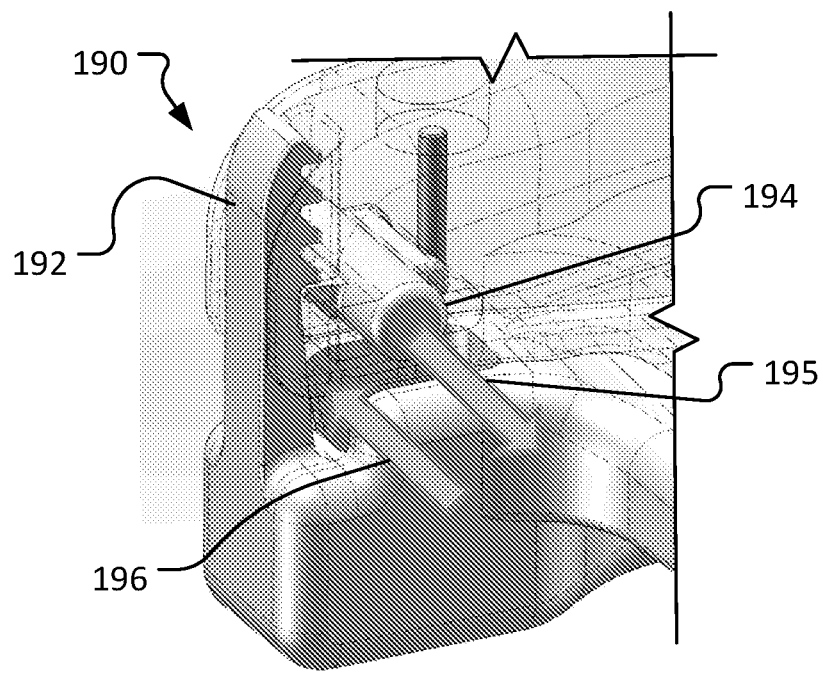

Referring also to FIGS. 14 and 15, clamp members 176a and 176b can be releasably detained in various orientations to each other using a height-adjustable latch mechanism 190. Height-adjustable latch mechanism 190 includes a multi-toothed latch member 192 and a latch member 194.

To release height-adjustable latch mechanism 190, a force (as depicted by arrow 195) can be applied to latch member 194. Force 195 will disengage latch member 194 from multi-toothed latch member 192. Then, clamp members 176a and 176b are released to be pivoted in relation to each other about adjustable hinge pin 172.

To latch height-adjustable latch mechanism 190, a force (as depicted by arrow 196) can be applied to latch member 194 so that latch member 194 returns to its home position in which latch member 194 can be engaged with multi-toothed latch member 192. Then clamp members 176a and 176b can be pivoted toward each other. As clamp members 176a and 176b are pivoted to reach an opposing relationship with each other, latch member 194 will become engageable with multi-toothed latch member 192. Latch member 194 can be selectively engaged with any teeth of multi-toothed latch member 192.

The disclosure of U.S. patent application Ser. No. 15/040,364 is hereby incorporated by reference in its entirety for all purposes. Accordingly, one or more design features described in the context of the penile traction devices disclosed in U.S. patent application Ser. No. 15/040,364 can be alternatively or additionally included in the penile traction device embodiments described herein. That is, one or more features of the penile traction devices disclosed in U.S. patent application Ser. No. 15/040,364 can be mixed and matched with one or more features of the penile traction device embodiments described herein to create hybrid designs. For example, features of the penile traction devices disclosed in U.S. patent application Ser. No. 15/040,364 that are directed to aspects such as, but not limited to, adjustability, modularity, force measurement, tensioning, contralateral traction, clamping, and the like, can be alternatively or additionally included in the penile traction device embodiments described herein. Any and all such hybrid designs and combinations of features are within the scope of this disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A penile traction device for applying traction force to a penis of a human body, the device comprising:
   a base, the base including a surface configured for interfacing with the human body while the traction force from the penile traction device is being applied to the penis;
   a longitudinally-adjustable portion extending from the base, the longitudinally-adjustable portion being spring-loaded for applying a longitudinal traction force to the penis; and
   a pivotable portion extending from the longitudinally-adjustable portion, the pivotable portion being selectively pivotable in relation to the longitudinally-adjustable portion, the pivotable portion including a clamp for releasably clamping a distal portion of the penis to the penile traction device.

2. The device of claim 1, wherein the base defines a clearance hole through which the penis can extend.

3. The device of claim 1, wherein the longitudinally-adjustable portion comprises:
   a first stage of longitudinal length adjustability; and
   a second stage of longitudinal length adjustability, wherein the first stage of longitudinal length adjustability is adjustable in length independent of the second stage of longitudinal length adjustability.

4. The device of claim 3, wherein the second stage of longitudinal length adjustability includes one or more springs such that the longitudinally-adjustable portion is spring-loaded.

5. The device of claim 4, wherein the second stage of longitudinal length adjustability includes a mechanism for releasably latching the second stage of longitudinal length adjustability in a retracted configuration.

6. The device of claim 5, wherein, while the second stage of longitudinal length adjustability is latched in the retracted configuration, the one or more springs are inactive such that the one or more springs do not apply the longitudinal traction force, and wherein, while the second stage of longitudinal length adjustability is unlatched from the retracted configuration, the one or more springs actively apply the longitudinal traction force.

7. The device of claim 4, wherein the one or more springs apply the longitudinal traction force in a direction perpendicular to the surface of the base.

8. The device of claim 1, wherein the pivotable portion is selectively pivotable in relation to the longitudinally-adjustable portion along a range of adjustment of 120 degrees.

9. The device of claim 8, wherein the pivotable portion is detainable in three or more differing angular relationships in relation to the longitudinally-adjustable portion.

10. The device of claim 1, wherein the clamp is selectively adjustable between two or more detent positions that apply differing degrees of clamping force to the penis.

11. The device of claim 10, wherein the clamp comprises a first clamp member with a first clamp surface and a second clamp member with a second clamp surface that opposes the first clamp surface.

12. The device of claim 11, wherein the clamp is selectively adjustable such that at each of the two or more detent positions the first and second clamp surfaces oppose each other a consistent angle.

13. A method of applying traction force to a penis, wherein the method comprises:
   coupling a penile traction device of any one of claims 1 through 12 to the penis; and
   applying the traction force to the penis using the device.

14. The method of claim 13, wherein the traction force is applied subsequent to coupling the device to the penis.

15. The method of claim 13, wherein the traction force is a dynamic-loading traction force.

* * * * *